United States Patent
Albrecht et al.

(10) Patent No.: US 7,309,322 B2
(45) Date of Patent: Dec. 18, 2007

(54) DEVICE FOR APPLYING A VENTRALLY OR DORSALLY DIRECTED TRANSLATORY FORCE IN THE AREA OF A KNEE JOINT

(75) Inventors: Erich Albrecht, Neubeuem (DE); Hans-Georg Opahle, Rosenheim (DE)

(73) Assignee: Albrecht GmbH, Neubeuern (DE)

( * ) Notice: Subject to any disclaimer, the term of this patent is extended or adjusted under 35 U.S.C. 154(b) by 295 days.

(21) Appl. No.: 10/538,047

(22) PCT Filed: Feb. 13, 2003

(86) PCT No.: PCT/EP03/01456

§ 371 (c)(1),
(2), (4) Date: Jun. 8, 2005

(87) PCT Pub. No.: WO2004/056293

PCT Pub. Date: Jul. 8, 2004

(65) Prior Publication Data

US 2006/0116616 A1     Jun. 1, 2006

(30) Foreign Application Priority Data

Dec. 19, 2002   (DE) .............................. 102 59 751

(51) Int. Cl.
*A61F 5/00*  (2006.01)
(52) U.S. Cl. ............................ 602/23; 602/26; 128/882
(58) Field of Classification Search ................ 602/5, 602/23, 26; 128/882
See application file for complete search history.

(56) References Cited

U.S. PATENT DOCUMENTS

| | | | | | |
|---|---|---|---|---|---|
| 1,072,369 | A | * | 9/1913 | Spahn | 602/16 |
| 2,877,033 | A | * | 3/1959 | Koetke | 403/95 |
| 5,063,917 | A | * | 11/1991 | Young et al. | 602/26 |
| 5,421,810 | A | * | 6/1995 | Davis et al. | 602/16 |
| 5,885,235 | A | * | 3/1999 | Opahle et al. | 602/16 |
| 5,954,677 | A | * | 9/1999 | Albrecht et al. | 602/16 |

FOREIGN PATENT DOCUMENTS

| | | |
|---|---|---|
| DE | 297 05 405 | 5/1997 |
| DE | 196 45 076 | 5/1998 |
| EP | 1 114 619 | 7/2001 |
| FR | 2 723 842 | 3/1996 |

* cited by examiner

Primary Examiner—Michael A. Brown
(74) Attorney, Agent, or Firm—Nixon & Vanderhye P.C.

(57) ABSTRACT

A device for applying a ventrally or dorsally directed translatory force onto a lower leg in the area of the knee joint includes a thigh bar and a lower leg bar device having a shorter and a longer bar arm. Both bar arms can be freely swiveled relative to the thigh bar. The two bar arms are disposed in such a manner that they can be swiveled relative to each other. A pretension of a spring device between the shorter and the longer bar arm has the effect that the bar arms are urged to carry out a swiveling motion relative to each other, thereby applying a ventrally or dorsally directed translatory force onto a lower leg fixation device in an area close to the knee.

9 Claims, 6 Drawing Sheets

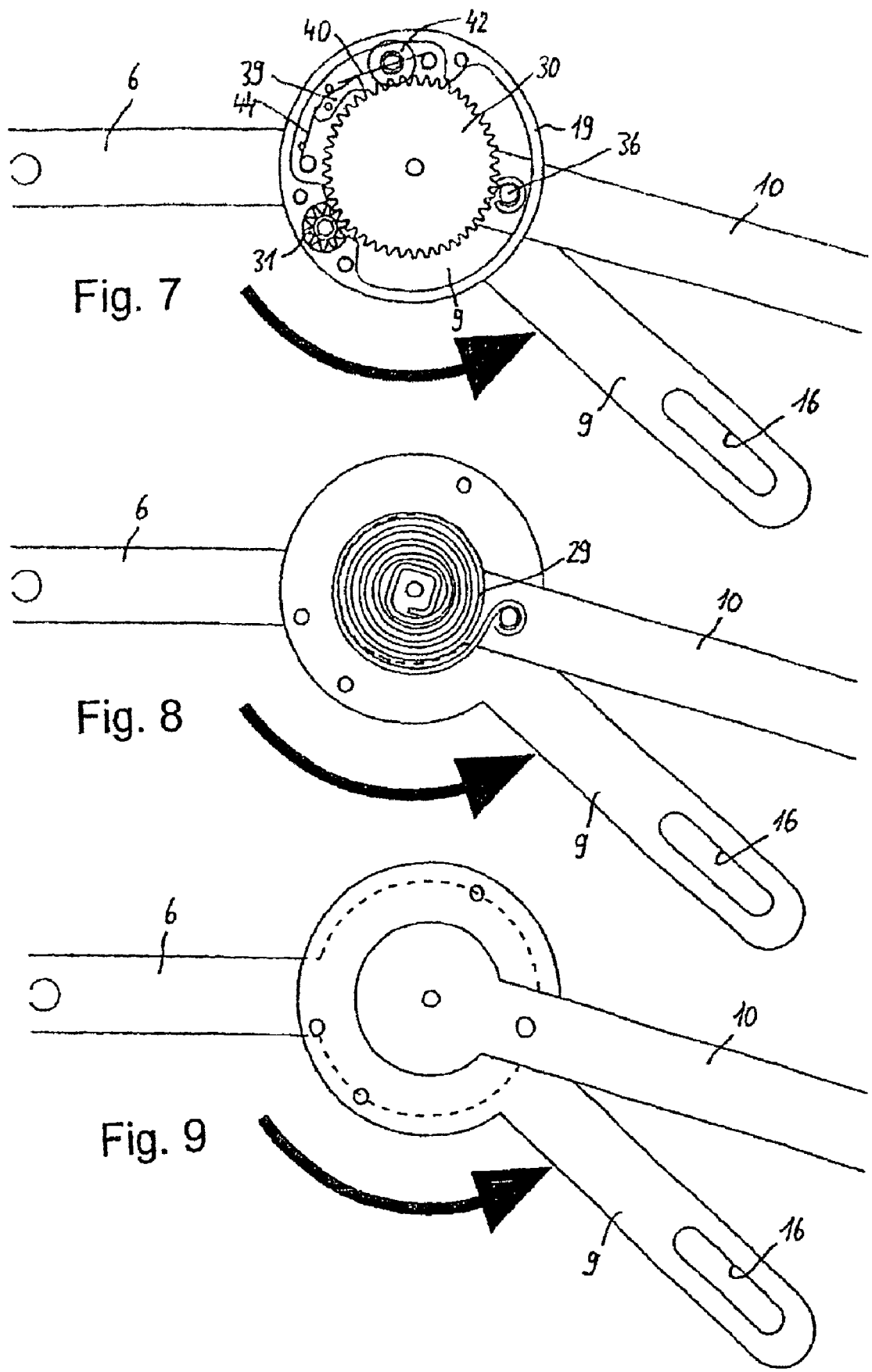

DEVICE FOR APPLYING A VENTRALLY OR DORSALLY DIRECTED TRANSLATORY FORCE IN THE AREA OF A KNEE JOINT

This application is the US national phase of international application PCT/EP2003/001456 filed 13 Feb. 2003 which designated the U.S. and claims benefit of DE 102 59751.0, filed 19 Dec. 2002, the entire contents of each of which are hereby incorporated by reference.

BACKGROUND OF THE INVENTION

The invention relates to a device for applying a ventrally or dorsally directed translatory force onto a lower leg in the area of a knee joint for treatment or follow-up treatment of knee instability, in particular cruciate ligament instability.

In the field of knee instability, posterior cruciate ligament lesions in particular pose considerable medical problems. Although there are well proven surgical reconstruction procedures for posterior cruciate ligament ruptures and other lesions of the posterior cruciate ligaments, the result of surgery has often deteriorated after a few months, or been lost altogether, because the sutured or reconstructed ligament has been stretched again in an undesired manner on account of the gravitational force of the lower leg which, with the patient lying on his back, acts in the dorsal direction. This leads to incorrect positioning of the tibia relative to the femur, as is indicated by broken lines in FIG. 1. By contrast, the solid lines in FIG. 1 show the tibia and the lower leg in the normal state. The risk of this kind of incorrect positioning, i.e. dropping of the tibia relative to the femur, also arises of course when a posterior cruciate ligament lesion is treated, not surgically, but by conservative methods.

In the case of anterior cruciate ligament instability, a problem which may occur is that the tibia comes to lie too far in the ventral direction relative to the femur. This is especially the case when the articular surface of the patient's tibia is inclined in such a way that, in the upright position in which the femur presses on the oblique articular surface of the tibia, a force is exerted in the ventral direction on the tibia. If the anterior cruciate ligament is unstable, the tibia in the area of the knee joint is displaced forward in an undesired manner, i.e. upward as shown in FIG. 1.

A device is already known for applying a ventrally or dorsally directed translatory force onto the lower leg in the area of the knee joint, which device is intended to counteract this undesired shifting of the tibia. This known device has thigh bars which are arranged medially and laterally in the area of the thigh and which can be secured on the thigh by means of a cuff. A swivel lever is mounted in an articulated manner at the distal end of the thigh bars which are located laterally alongside the knee, which swivel lever is pretensioned either in the ventral direction or in the dorsal direction by means of a spring. This swivel lever engages under or over a bolt protruding laterally from a lower-leg cuff in an area of the lower leg close to the knee. Depending on how the pretensioning of the spring is directed, the upper end of the tibia is urged either in the ventral direction or the dorsal direction in order to counteract an undesired stretching of a damaged posterior or anterior cruciate ligament and an associated translatory displacement of the tibia in the dorsal or ventral direction. A problem with this known device, however, is that the spring force on the lower leg means that a permanent force is exerted in the extension direction or flexion direction, i.e. a torque which seeks to permanently extend or flex the lower leg. A free and unimpeded extension or flexion of the knee is therefore not possible with this known device.

SUMMARY OF THE INVENTION

Starting out from this, the object of the invention is to make available a device of the type mentioned at the outset which, in a particularly effective way, prevents undesired displacement of the tibia in the dorsal direction or ventral direction and permits free mobility of the knee joint.

According to the invention, this object is achieved by the embodiments described herein.

The device according to the invention has the following features:

- the lower-leg bar device has a shorter bar arm and a longer bar arm, both bar arms being able to swivel relative to the thigh bar,
- the two bar arms are arranged so as to be able to swivel relative to one another,
- the shorter bar arm is coupled at its distal end to the fixation device in an area close to the knee, whereas the longer bar arm is coupled with its distal end to the fixation device in an area farther away from the knee,
- the pretensioning force of the spring device acts between the shorter and longer bar arms in such a way that the bar arms are urged to execute a swiveling movement relative to each other, such that a ventrally or dorsally directed translatory force is applied to the fixation device in the area close to the knee.

It is thus a characteristic of the device according to the invention that the spring force does not act between the thigh bar and the lower-leg bar device, but instead between the two bar arms which extend from the knee-joint area in the distal direction alongside the lower leg and, because of their different lengths, are coupled to the lower-leg fixation device with their distal ends at different locations. In this way, a torque is exerted on the fixation device, and thus on the lower leg, and urges the tibia, in the area close to the knee joint, either into the ventral direction or the dorsal direction depending on the direction of the spring force and the arrangement of the bar arms. By contrast, both lower-leg bar arms are mounted on the distal end of the thigh bar so as to be able to swivel freely relative to the thigh bar, i.e. no spring force acts between the thigh bar on the one hand and the two lower bar arms on the other. The patient is therefore able to flex or extend his knee without additional force being applied.

According to an advantageous embodiment, at least one of the bar arms has, at its distal end, an oblong hole into which a bolt of the fixation device protrudes, in order to couple the bar arm to the fixation device in a longitudinally displaceable manner. This takes account of the fact that the distances between the swivel axis of the device and the two coupling points where the lower-leg bar arms engage on the fixation device may vary depending on the swivel position of the fixation device. The longitudinally displaceable coupling of the at least one bar arm on the fixation device thus does not obstruct the swiveling movement of the fixation device by means of the two bar arms. As an alternative to an oblong hole, however, it would also be entirely possible to place the bar arm concerned onto the relevant bolt only from one side, so that this bar arm presses against the bolt from one side.

The fixation device which can be secured on the lower leg is expediently made up of a half-shell, and the two bar arms are coupled to the half-shell at the two opposite end areas of the half-shell.

According to an advantageous embodiment, the spring device comprises a flat coil spring arranged in a spring housing which is secured on one of the bar arms and, together with the latter, can be swiveled relative to the thigh bar. The center axis of the spring housing in this case expediently coincides with the swivel axis. This permits a particularly simple and space-saving configuration.

It is also expedient if, for adjusting the desired translatory force, the pretensioning force of the spring device can be adjusted by means of a toothed gear wheel located in the spring housing.

According to an advantageous embodiment, the lower-leg bar device is mounted in an oblong hole of the thigh bar so as to be displaceable on the thigh bar. In this way, the lower-leg bar device can, in addition to the swiveling movement, also execute a translatory movement relative to the thigh bar and in this way can optimally follow the path of movement during flexion and extension of the knee, without unpleasant tension or compression stresses arising on the thigh cuff along the thigh. For this purpose, the oblong hole expediently extends in the longitudinal direction of the thigh bar.

BRIEF DESCRIPTION OF THE DRAWINGS

The invention is explained in more detail below by way of example with reference to the drawings, in which:

FIGS. 7 to 9 show a plan view of the device according to the invention from the planes VII, VIII and IX as indicated in FIG. 4.

DETAILED DESCRIPTION OF THE INVENTION

Figure 1:
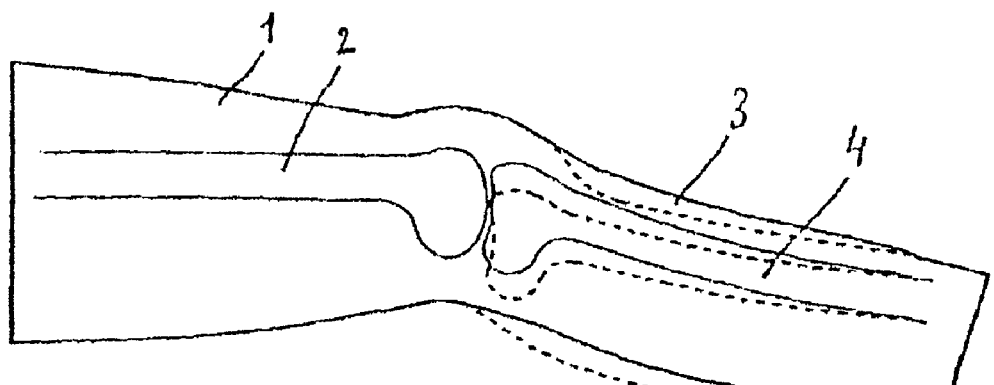
FIG. 1 shows a schematic representation of a human leg in the area of the knee joint with femur and tibia, the lower leg and tibia being shown in the normal position and in a dorsally displaced position.

A thigh 1 with femur 2 and a lower leg 3 with tibia 4 can be seen in FIG. 1. Here, solid lines indicate the normal position of the lower leg 3 and tibia 4, and broken lines indicate a dorsally dropped position of the lower leg 3 and tibia 4, as may arise in cases of cruciate ligament instability, because of the dorsally acting gravitational force when a patient is lying on his back.

Figure 2A:
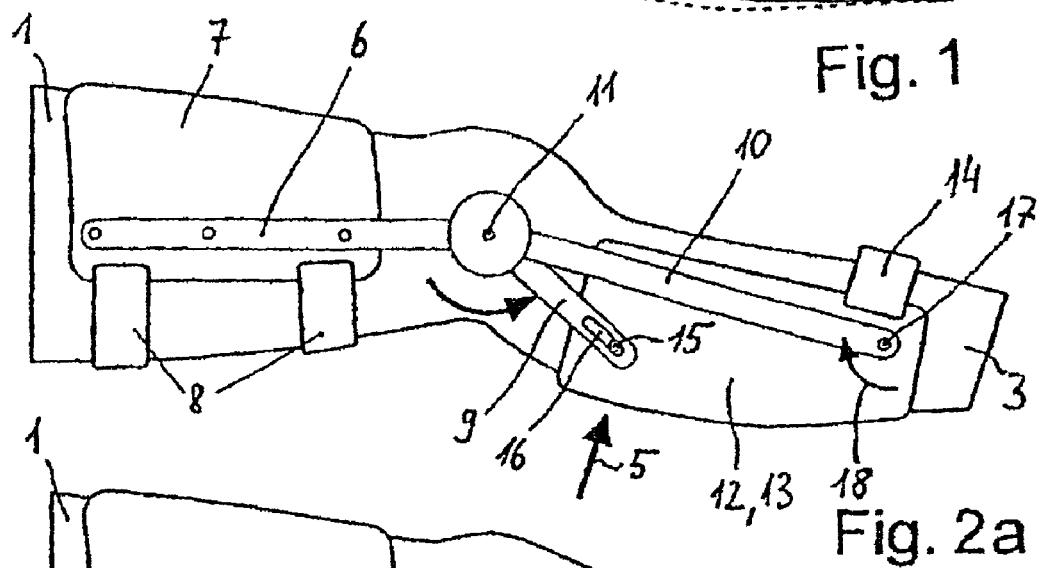
FIGS. 2a to 2c show side views of a first embodiment of the device according to the invention placed on the leg, with different angle settings of the lower-leg bar arms in order to elucidate the function of the invention.
Figure 2B:
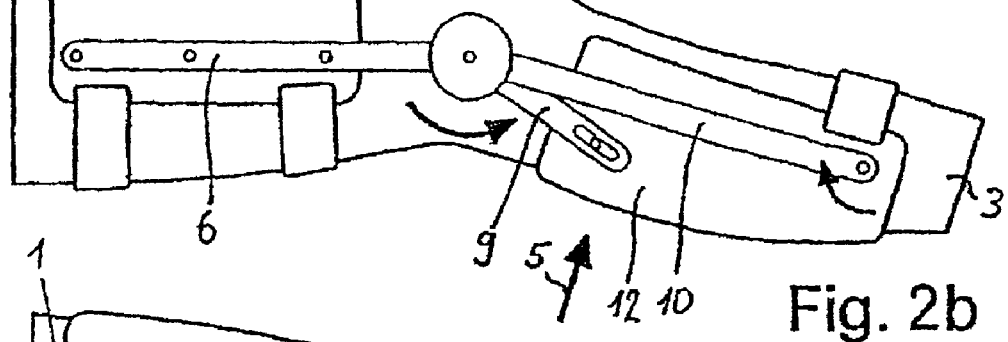
Figure 2C:
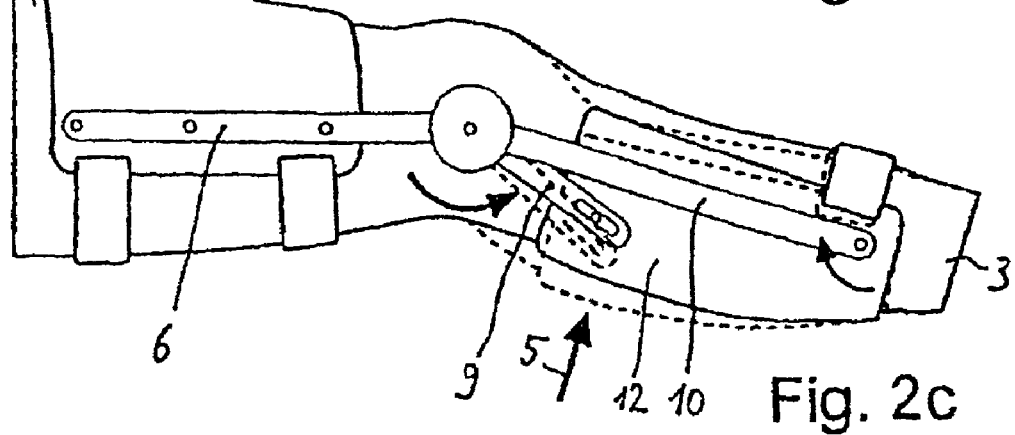

FIGS. 2a to 2c show a device in the form of an orthosis with which a ventrally directed translatory force counteracting the dropping of the tibia can be applied onto the lower leg 3 in an area close to the knee, so that dropping of the tibia 4 can be prevented from the outset, even in cases of weakened cruciate ligaments, or so that a dropping of the tibia 4 can be rectified. The direction of the translatory force applied by the orthosis is indicated here by the arrow 5. FIG. 2a shows the orthosis fitted on a leg, where the lower leg 3 is in a dropped state. FIG. 2b again shows the normal position of the lower leg, which is obtained by means of the translatory force applied by the orthosis. The broken lines and solid lines in FIG. 2c once again indicate the positions of the lower leg 3 and of the orthosis as shown in FIGS. 2a and 2b, to permit direct comparison of the two states.

In FIGS. 2a to 2c, only the bar arrangement located on one side of the leg can be seen. The entire orthosis, however, is made up of two such bar arrangements which extend laterally and medially alongside the leg and are arranged with mirror symmetry in relation to one another. It is also conceivable, however, for such a bar arrangement to be provided on just one side of the leg.

FIGS. 2a to 2c show a thigh bar 6 which can be secured on the thigh 1 by means of a cuff 7. The cuff 7 is expediently made up of a half-shell which is placed on the front of the thigh and which can be fixed on the thigh 1 by means of straps 8 which are guided around the back of the thigh and have velcro-type fasteners. In the distal end area of the thigh bar 6, located laterally alongside the knee joint, a shorter bar arm 9 and a longer bar arm 10 extending in the direction of the lower leg 3 are mounted so as to be able to swivel.

The swivel axis is indicated by 11. Both bar arms 9, 10, which together are designated here as lower-leg bar device, are able to swivel freely relative to the thigh bar 6, i.e. no spring force acts between the thigh bar 6 on the one hand and the lower-leg bar device on the other hand. By contrast, a spring force does act between the shorter bar arm 9 and the longer bar arm 10, and this spring force seeks to turn the shorter bar arm 9 counterclockwise and the longer bar arm 10 clockwise.

The two distal ends of the bar arms 9, 10 act on a fixation device 12 consisting of a half-shell 13 which is arranged dorsally, i.e. in the calf area, and which extends along the lower leg 3 in the distal direction from an area close to the knee. The half-shell 13 is secured on the lower leg 3 by means of a retaining strap 14 which has a velcro-type fastener.

As can be seen from FIGS. 2a to 2c, the distal end of the shorter bar arm 9 is coupled to a bolt 15 which protrudes laterally outward from the fixation device 12 in the end area of the fixation device 12 close to the knee. For this purpose, the shorter bar arm 9 has an oblong hole 16 into which the bolt 15 engages. The bar arm 9 is thus guided in a longitudinally displaceable manner on the bolt 15 by means of this oblong hole 16.

At its distal end, the longer bar arm 10 is mounted so as to be able to swivel on a bolt 17 in a distal end area of the fixation device 12. The half-shell 13 can thus be swiveled about the bolt 17, as is indicated by the arrow 18. Because of the distance between the bolts 15 and 17 in the longitudinal direction of the lower leg 3, the half-shell 13 thus executes a swiveling or tilting movement in the clockwise direction and thereby exerts the desired translatory force on the tibia 4 in the ventral direction.

Referring to FIGS. 3 to 9, the structure of the bar arrangement shown in FIGS. 2a to 2c will now be explained in more detail below.

Figure 3:
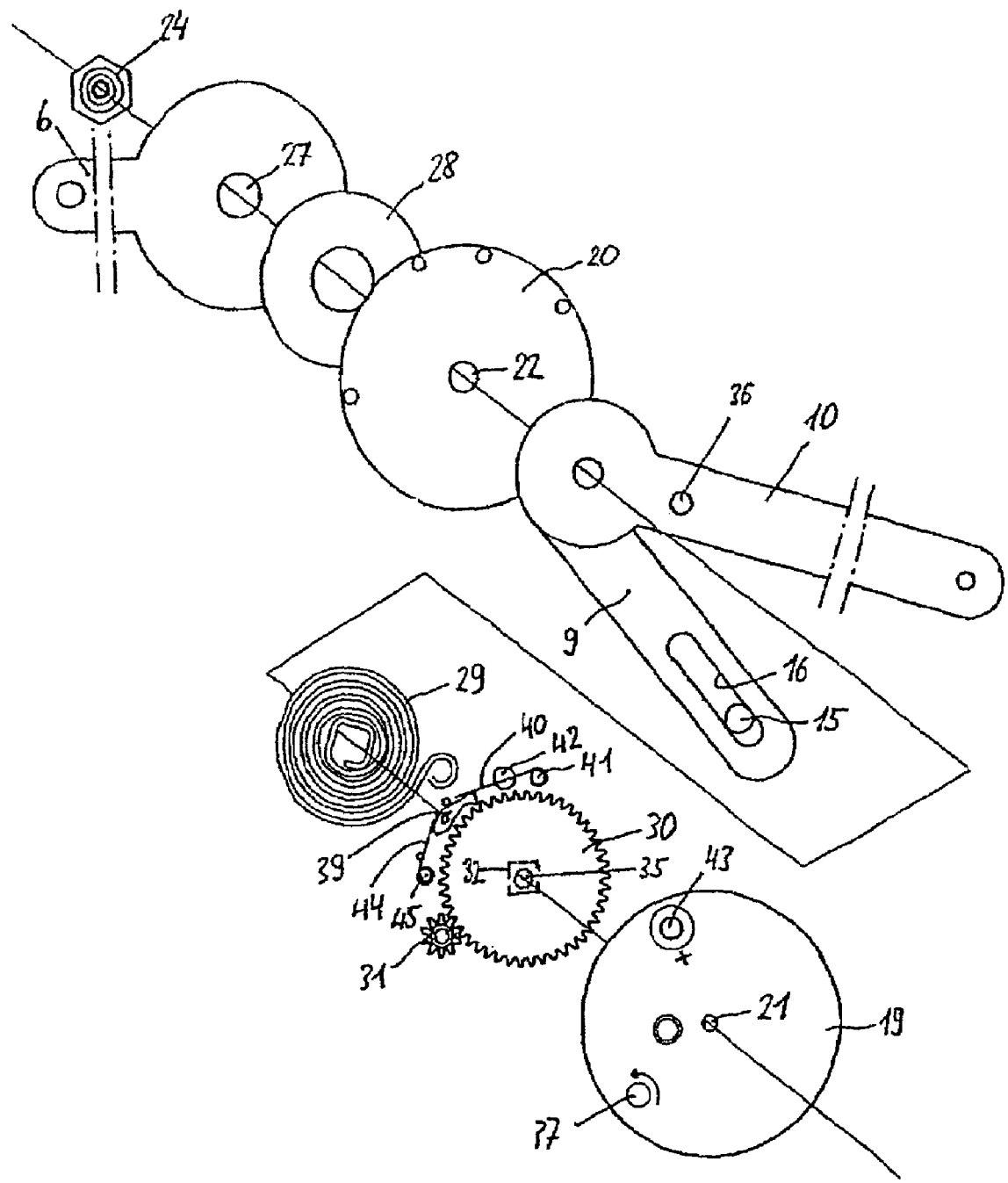
FIG. 3 shows an exploded view of the most important individual parts of the device from FIGS. 2a to 2c.
Figure 4:
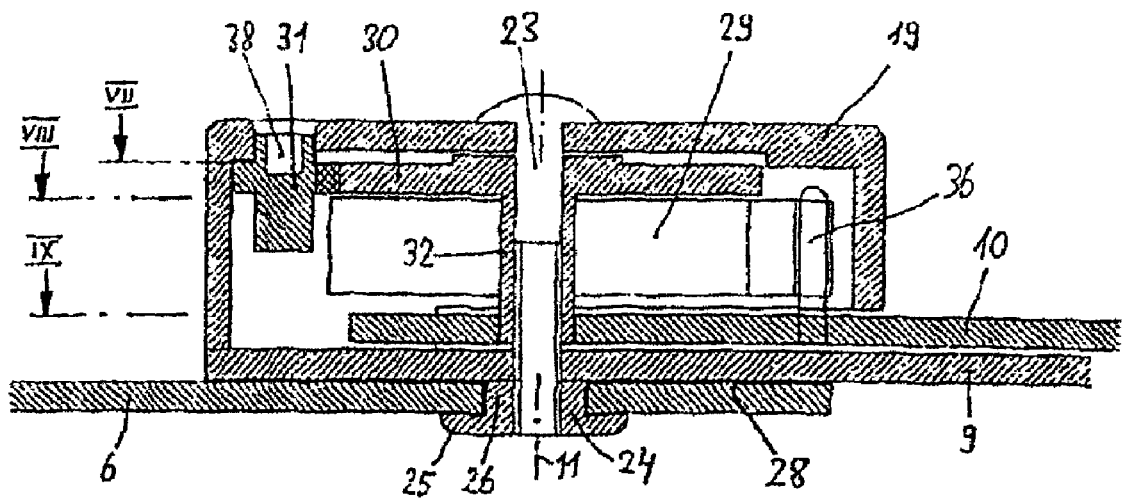
FIG. 4 shows a cross section through the device according to the invention in the area of the spring housing.
Figure 5A:
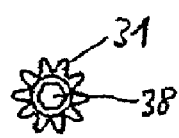
FIGS. 5a and 5b show a plan view and side view, respectively, of the driving toothed wheel for tensioning the spring.
Figure 6A:
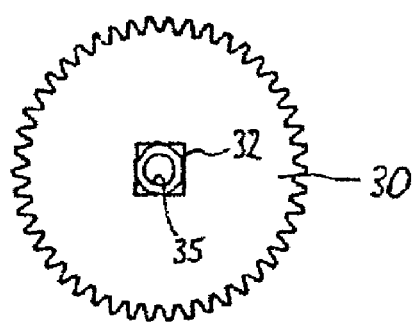
FIGS. 6a and 6b show a plan view and side view, respectively, of the toothed wheel for tensioning the spring.
Figure 5B:
Figure 6B:
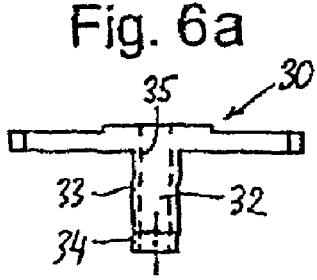

As can be seen from FIGS. 3 and 4, this bar arrangement comprises, in the area of the bar hinge, a bowl-shaped spring housing 19 which is screwed onto the proximal end area of the shorter bar arm 9 and is therefore connected fixedly to the latter.

The proximal end area of the shorter bar arm 9 is designed as a circular disk 20 whose external diameter corresponds to the external diameter of the spring housing 19. The spring housing 19 and the bar arm 9 each have a central through-hole 21, 22, respectively, through which a screw 23 can be guided. The screw 23 is provided with a thread onto which a nut 24 can be screwed until it bears on the bar arm 9. The screw 23 and the nut 24 are thus secured in position relative to the spring housing 19 and bar arm 9.

The nut 24 has a hexagonal head 25 and an axially protruding cylindrical collar 26 with a smaller external diameter than the head 25. This cylindrical collar 26 serves as a rotation bearing for the thigh bar 6 which, for this purpose, has, in its distal end area, a central through-hole 27 whose diameter is adapted to the external diameter of the cylindrical collar 26. A friction-reducing disk 28, in particular made of Teflon, is arranged between the thigh bar 6 and the shorter bar arm 9. It will be seen that, by virtue of this arrangement, the shorter bar arm 9 together with the spring housing 19 can be swiveled freely about the swivel axis 11.

As will be seen from FIGS. 3 and 4, a spring in the form of a flat coil spring 29 is arranged inside the spring housing 19, this spring being used to generate a pretensioning force acting between the shorter bar arm 9 and the longer bar arm 10. As will be explained in more detail below, this flat coil spring 29 cooperates with a toothed wheel gear which is likewise arranged inside the spring housing 19 and which is made up of a central toothed wheel 30 and of a peripheral driving toothed wheel 31 of smaller diameter meshing with the toothed wheel 30. The central toothed wheel 30, which is shown in more detail in FIGS. 6a and 6b, has a central, axial protrusion 32 which, along most of its length, i.e. in the area 33, has a square cross section on the outside. The end area 34 of the protrusion 32 is, by contrast, cylindrical on the outside and serves as a rotation bearing for the longer bar arm 10 (see FIG. 10). The bar arm 10, which extends through a recess in the circumferential wall of the spring housing 19, is thus able to swivel about the protrusion 32.

The central toothed wheel 30 also has a central, axial bore 35 through which the screw 23 can be guided. The screw 23 thus serves as a rotation bearing for the central toothed wheel 30.

As will be seen from FIGS. 3 and 8, the flat coil spring 29 is bent in a square shape in its inner end area in such a way that it can be fitted with slight play onto the square protrusion 32 of the central toothed wheel 30. The inner end of the flat coil spring 29 is thus secured in a rotationally fixed manner on the protrusion 32. The outer end of the flat coil spring 29 is connected to an axially disposed coupling pin 36 which is secured on the longer bar arm 10.

By means of this arrangement, the pretensioning force of the spring 29 thus acts between the central toothed wheel 30 and the longer bar arm 10. The pretensioning force of the spring 29 can in this case be altered by turning the toothed wheel 30, this being effected via the driving toothed wheel 31. The driving toothed wheel 31 is turned manually using a hexagon key which can be introduced through a bore 37 in the spring housing 19 and can be brought into engagement with a hexagon-shaped recess 38 in the driving toothed wheel 31.

Undesired turning of the central toothed wheel 30 relative to the spring housing 19 is prevented by means of a catch 39 (FIGS. 3 and 7) which is in engagement with the teeth of the toothed wheel 30. The catch 39 is mounted (in a manner not shown) in the spring housing 19 in such a way as to be able to swivel. A spring tongue 40, secured on a retaining bolt 41 of the spring housing 19, presses on the catch 39 from outside in such a way that its free end in normal circumstances remains in engagement with the teeth of the toothed wheel 30 and prevents the toothed wheel 30 from turning back because of the pretensioning force of the flat coil spring 29. However, the spring tongue 40 can be lifted from the catch 39 by means of an eccentric 42, which eccentric 42 protrudes through an opening 43 in the spring housing 19 and can thus be actuated manually. If the spring tongue 40 is lifted from the catch 39, a further spring tongue 44, which presses from outside on the opposite end area of the catch 39, can disengage the catch 39 from the teeth, so that the toothed wheel 30 can be turned back and the pretensioning force can be reduced. The spring tongue 44 is also secured on the spring housing 19 by means of a retaining bolt 41.

When the catch 39 is engaged, the central toothed wheel 30 is thus securely coupled in one direction to the spring housing 19 via this catch 39, and thus to the shorter bar arm 9. The spring force of the flat coil spring 39 thus acts, on the one hand, on the central toothed wheel 30 via the square protrusion 32 and, from the central toothed wheel 30, on the shorter bar arm 9 via the catch 39 and the spring housing 19, and, on the other hand, on the longer bar arm 10 via the coupling pin 39.

In the illustrative embodiment shown, the flat coil spring 29 seeks to swivel the shorter bar arm 9 upward, i.e. counterclockwise, and the longer bar arm 10 downward, i.e. clockwise, such that a translatory force is applied in the ventral direction to the tibia in the area close to the knee. The device thus constitutes a so-called PCL bar. It will be noted that, alternatively to this, the application of a translatory force in the dorsal direction is possible in a simple way by reversing the direction of action of the flat coil spring 29 and the catch 39, by which means the device can be used as an ACL bar.

Figure 10:
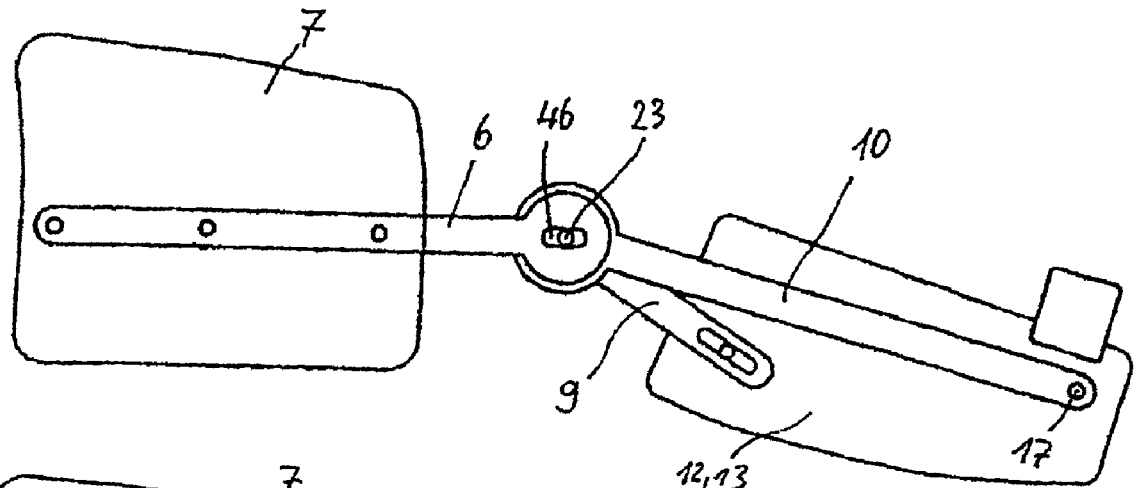
FIG. 10 shows a side view of a second embodiment of the device according to the invention, said device being situated substantially in an extension position.
Figure 11:
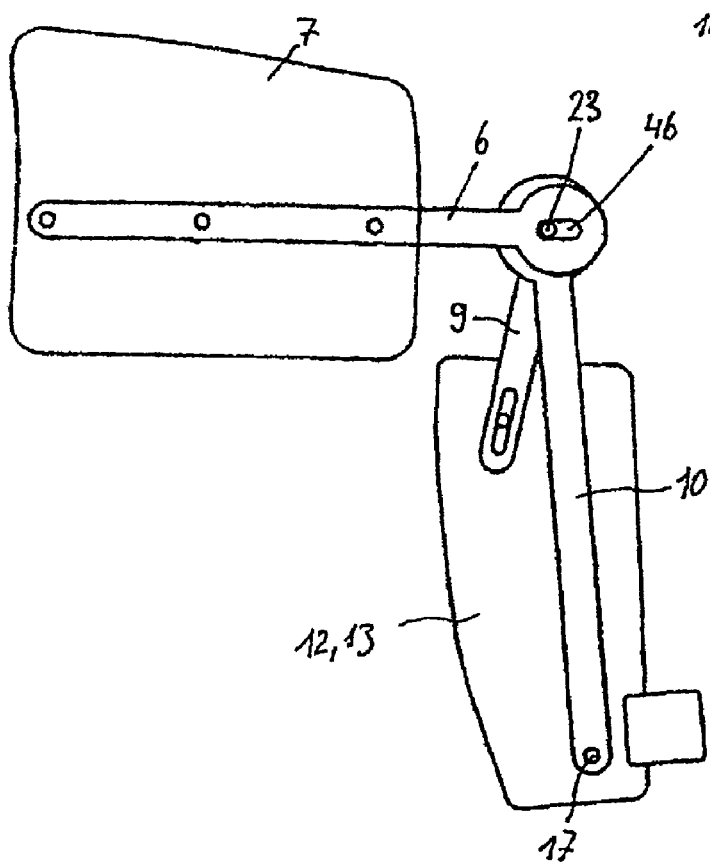
FIG. 11 shows the device from FIG. 10 in the flexion position.
Figure 13:
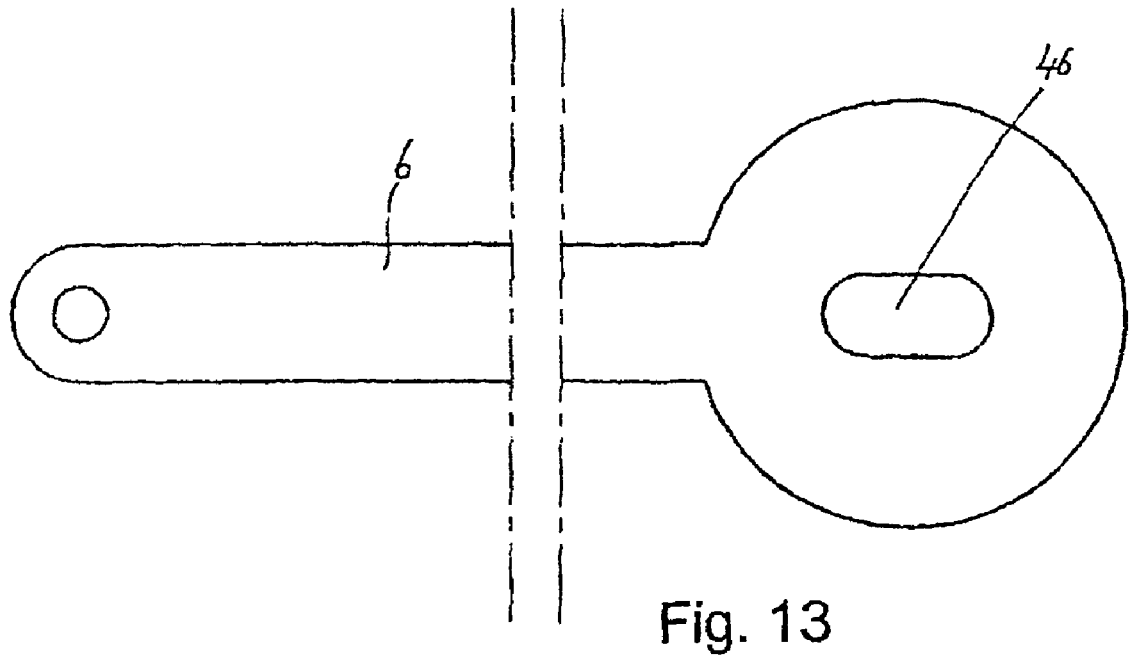
FIG. 13 shows a shortened side view of the thigh bar, with oblong hole, used in the second embodiment.

FIGS. 10 and 11 show a second embodiment of the device according to the invention in which the thigh bar 6, in the hinge area, has an oblong hole 46 extending in the longitudinal direction of the thigh bar 6. The thigh bar 6 is shown on its own in FIG. 13. The oblong hole 46 means that the screw 23 serving as swivel axis, and thus the entire lower-leg bar device, can move together with the spring housing 19 by a defined distance along the oblong hole 46.

Figure 12:
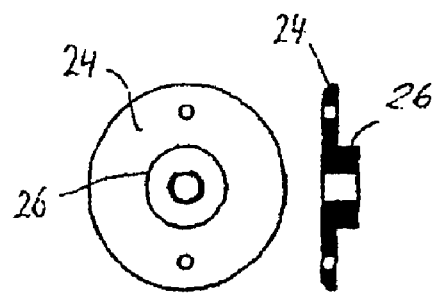
FIG. 12 shows a side view and a longitudinal section through the nut used in the second embodiment.

The nut 24 used in this embodiment is shown in FIG. 12. Like the nut in the first embodiment, this nut 24 again has a cylindrical collar 26 which engages in the oblong hole 46 and is guided by the long side walls of the oblong hole 46 with slight play. The other parts of the second embodiment are identical to those of the first embodiment and are therefore not described again in detail here.

The way in which the second embodiment works is identical to that of the first embodiment. The shorter bar arm 9 is moved in the arrow direction (see FIGS. 2a to 2c) toward the longer bar arm 10 by the force of the flat coil spring 29. In this way, the half-shell 13, i.e. the lower-leg shell, is swiveled about the distal coupling point 17 and pressed ventrally in the end area close to the knee joint, such that the tibia is pushed forward relative to the femur.

This causes a reaction force which presses the end area of the lower-leg bar device in the dorsal direction in the hinge area. Since the thigh bar 6, however, is fixed securely on the thigh via the cuff 7, the hinge area of the device is held in a fixed position relative to the knee joint. Upon flexion of the knee joint, however, the force acting in the hinge area seeks to displace the cuff 7 of the thigh slightly in the proximal direction. Upon subsequent extension, by contrast, a tension stress, possibly felt to be unpleasant, would be exerted on the thigh bar 6 if the lower-leg bar device were mounted non-displaceably on the thigh bar, as is the case in the first embodiment. However, the oblong hole 46, which is provided in the thigh bar 6 and is situated laterally and centrally alongside the knee joint, permits a displacement of the bearing along the oblong hole 46, such that tension or compression forces can be avoided in the longitudinal direction of the thigh.

The invention claimed is:

1. A device for applying a ventrally or dorsally directed translatory force onto a lower leg in the area of a knee joint for treatment or follow-up treatment of knee instability, the device comprising a thigh bar which can be secured on a thigh, with a lower-leg bar device, which acts on the lower leg, coupled in an articulated manner to the thigh bar and operatively connected to a fixation device that can be secured on the lower leg, and a spring device which generates a defined pretensioning force and acts on the lower-leg bar device, wherein:

the lower-leg bar device has a shorter bar arm and a longer bar arm, both bar arms being able to swivel relative to the thigh bar, the two bar arms are arranged so as to be able to swivel relative to one another, the shorter bar arm is coupled at its distal end to the fixation device in an area close to the knee, whereas the longer bar arm is coupled with its distal end to the fixation device in an area farther away from the knee, and the pretensioning force of the spring device acts between the shorter and longer bar arms in such a way that the bar arms are urged to execute a swiveling movement relative to each other, such that a ventrally or dorsally directed translatory force is applied to the fixation device in the area close to the knee.

2. The device as claimed in claim 1, wherein the two bar arms of the lower-leg bar device are able to swivel about the same swivel axis situated at the distal end of the thigh bar.

3. The device as claimed in claim 1, wherein the bar arms are coupled at their distal ends by means of bolts which extend laterally outward from the fixation device.

4. The device as claimed in claim 1, wherein at least one of the bar arms has, at its distal end, an oblong hole into which a bolt of the fixation device protrudes, in order to couple the bar arm to the fixation device in a longitudinally displaceable manner.

5. The device as claimed in claim 1, wherein the fixation device which can be secured on the lower leg is made up of a half-shell, and the two bar arms are coupled to the half-shell at opposite end areas of the half-shell.

6. The device as claimed in claim 1, wherein the spring device comprises a flat coil spring arranged in a spring housing which is secured on one of the bar arms and, together with the latter, can be swiveled relative to the thigh bar, the center axis of the spring housing coinciding with the swivel axis.

7. The device as claimed in claim 6, wherein the pretensioning force of the spring device can be adjusted by means of a toothed wheel gear located in the spring housing.

8. The device as claimed in claim 1, wherein the lower-leg bar device is mounted in an oblong hole of the thigh bar so as to be displaceable on the thigh bar.

9. The device as claimed in claim 8, wherein the oblong hole extends in the longitudinal direction of the thigh bar.

* * * * *